US006908306B2

(12) United States Patent
Bowman et al.

(10) Patent No.: US 6,908,306 B2
(45) Date of Patent: Jun. 21, 2005

(54) ORTHODONTIC DISTALIZING APPARATUS

(75) Inventors: Steven Jay Bowman, Kalamazoo, MI (US); Mauro Testa, Avigliana (IT); Aldo Carano, Taranto (IT)

(73) Assignee: American Orthodontics Corp., Sheboygan, WI (US)

( * ) Notice: Subject to any disclaimer, the term of this patent is extended or adjusted under 35 U.S.C. 154(b) by 0 days.

(21) Appl. No.: 09/999,269

(22) Filed: Nov. 15, 2001

(65) Prior Publication Data

US 2003/0091952 A1 May 15, 2003

(51) Int. Cl.$^7$ .................................................. A61C 3/00
(52) U.S. Cl. ................................ 433/18; 433/6; 433/21
(58) Field of Search ............................. 433/18, 19, 20, 433/21, 22, 5, 6, 7

(56) References Cited

U.S. PATENT DOCUMENTS

| | | | | |
|---|---|---|---|---|
| 4,713,000 A | * | 12/1987 | Rosenberg | 433/18 |
| 5,785,520 A | | 7/1998 | Carano et al. | 433/7 |
| 5,967,772 A | | 10/1999 | Gray | 433/7 |
| 6,220,856 B1 | | 4/2001 | Carano et al. | 433/7 |

OTHER PUBLICATIONS

Keles, Ahmet, "Maxillary Unilateral Molar Distalization With Sliding Mechanics: A Preliminary Investigation," *European Journal of Orthodontics*, vol. 23, pp. 507–515 (2001).

Celenza, Frank, D.D.S. et al., *Absolute Anchorage in Orthodontics: Direct and Indirect Implant–Assisted Modalities*, JCO, Inc., vol. 34, No. 7, 2000.

\* cited by examiner

*Primary Examiner*—John J Wilson
(74) *Attorney, Agent, or Firm*—Foley & Lardner LLP

(57) ABSTRACT

An orthodontic distalizing apparatus comprises at least one force generating element positioned intermediate a force dissipating element secured to the hard palate and/or alveolar ridge and a first tooth (e.g., a molar) that is being distalized. The at least one force generating element is positioned to apply a distalizing force on the molar in a direction substantially along a longitudinal axis of the dental arch and at a low level of the basal gingiva. The at least one force generating element may be configured to prevent inadvertent disassembly thereof during installation, adjustment and/or conversion of the apparatus between an active and a passive state. In addition, the at least one force generating element may be configured to be reversibly convertible between an active state and a passive state without requiring removal of the device from the patient's mouth. Moreover, the at least one force generating element may be configured to provide a continuous activation force of substantially constant magnitude during distalization of the molar. The apparatus may also be constructed so that the force dissipating element is connected to at least one anchoring tooth by a slidable coupling that absorbs all reaction forces transmitted substantially along a direction of the longitudinal arch. A second force dissipating element may be positioned intermediate the force dissipating element and a second tooth (e.g., a bicuspid) to facilitate the closing of any gaps that are created following distalization of the molar. A method of converting an orthodontic distalizing apparatus between an active and a passive state is also provided.

37 Claims, 9 Drawing Sheets

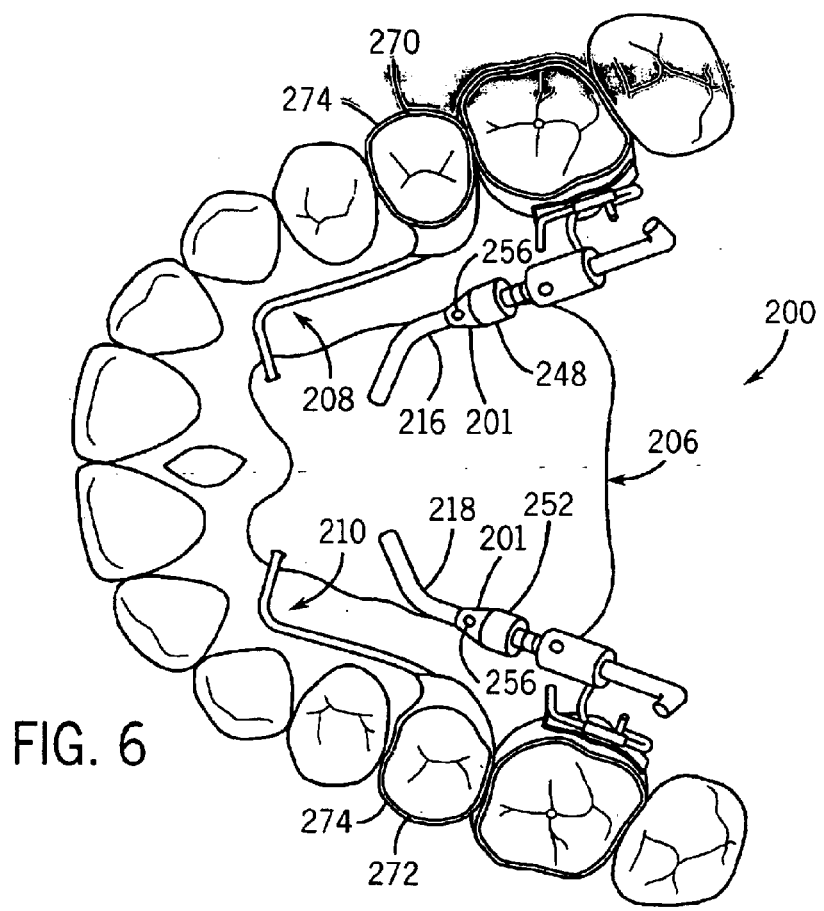
FIG. 6
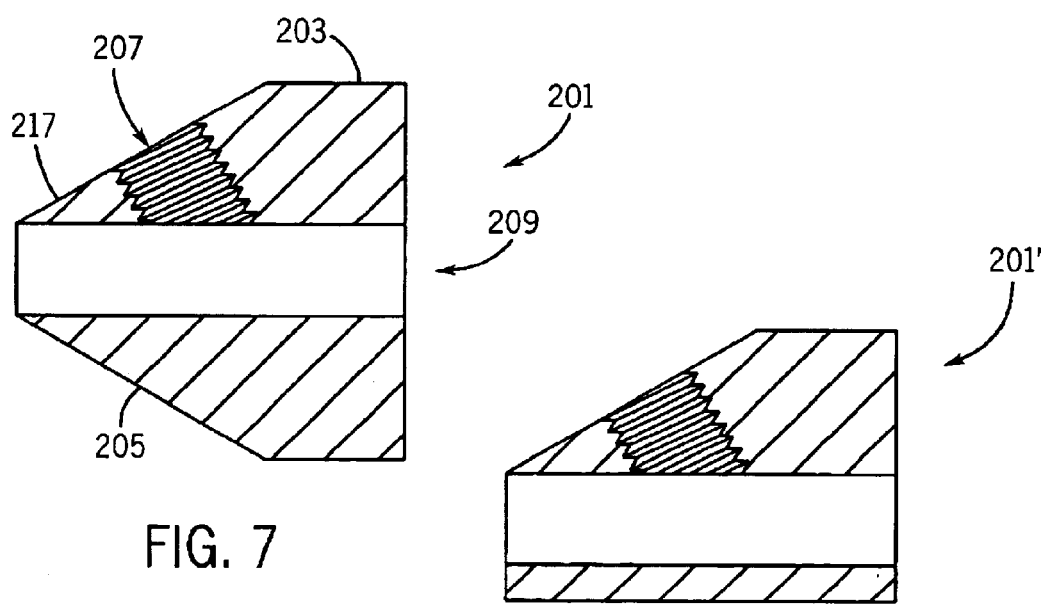
FIG. 7
FIG. 8

ORTHODONTIC DISTALIZING APPARATUS

FIELD OF THE INVENTION

The present invention relates to an orthodontic distalizing apparatus for correcting the relative position of the teeth.

BACKGROUND OF THE INVENTION

Orthodontic distalizing devices for correcting the relative position of the teeth of a dental arch are known. In such known devices of this kind, spring-loadable pusher means are generally arranged on the side opposite the lingual side of the dental arch. Moreover, the pusher means are interposed between the means for anchoring the framework to a tooth selected for that purpose and the means for fastening to the further tooth being distalized of the same branch of the dental arch. The reaction force exerted by the pusher on the tooth being distalized is not discharged completely onto the basal gingiva and underlying bony support of the arch, but can also act at least partially on the tooth selected for anchoring of the framework, thus resulting in the risk of causing displacement of the latter as well.

The pusher of the known distalizing apparatuses generally consists of a pusher pin which is fastened substantially tangentially to the tooth being distalized, and on which is mounted in coaxially sliding fashion a compression sleeve of a pusher spring. The spring is interposed between the head end of the pin, rigidly fastened to the means for fastening to the tooth being distalized, and the facing head end of the sliding sleeve. The latter is in turn joined to the anchoring means of the framework via wires or the like, with which it is held in the desired spring compression position. For this purpose the pusher pin must extend sufficiently beyond the anchoring tooth, in a direction opposite to the compression direction of the spring, as a result of which the pusher means have considerable dimensions and are thus retained non-rigidly or only in a direction opposite to the direction of spring compression on the anchoring tooth. The pusher pin therefore does not exert sufficiently precise directional guidance on the tooth to prevent the forces exerted by the pusher means from being expressed, even partially, as torques capable of causing tilting of the tooth from the correct vertical orientation and/or rotation thereof, and/or as components transverse to the longitudinal axis of the dental arch.

A number of relatively simple and low-cost designs which overcome all the above-identified drawbacks of conventional distalizing apparatuses are disclosed in U.S. Pat. No. 5,785,520, issued Jul. 28, 1998, which is hereby incorporated by reference in its entirety. According to one embodiment disclosed in the '520 patent, a distalizing apparatus 10 (illustrated in FIGS. 1–4 attached hereto) comprises a supporting framework 12 composed of an anatomical support element 14 (in the form of a Nance button) and a transverse structure 16 (in the form of a metal wire) embedded in Nance button 14. Framework 12 is anchored to a pair of anchoring teeth 18 and 20 by attaching the two opposed ends of transverse wire 16 to bands 22 and 24, respectively. Extending from Nance button 14 are two additional transverse structures 26 and 28 (also in the form of metal wires), both of which have ends joined by means of pusher elements 30 and 32 to bands 34 and 36, respectively, for fastening to teeth 38 and 40 being distalized.

In the illustrated embodiment, each pusher element 30, 32 generally comprises a pusher pin 42 and a narrow tube 44 that are telescopically engaged with one another (see FIG. 3), with an elastic element 46 (e.g., a compression spring as shown in FIGS. 1 and 2) captured therebetween. In addition, each pusher element includes a locking collar 48 that is slidably mounted on tube 44 so that compression spring 46 can be preloaded as desired by moving locking collar 48 towards or away from pusher pin 42 and locking it in position. Pusher elements 30 and 32 are assembled and installed in the dental arch with the proper position and orientation so that the forces generated thereby are exerted in the general direction of the longitudinal axis of the dental arch. During this installation process, the technician must take care when adjusting the position of locking collar 48 to ensure that pusher elements 30 and 32—including their associated springs and locking collars—remain in the fully assembled state to prevent the possibility of one or more elements being swallowed or aspirated.

As best seen in FIG. 2, the attachment points of pusher elements 30 and 32 to wires 26 and 28 are located as low as possible within the dental arch so that pusher elements 30 and 32 are within the basal zone of gingiva. Similarly, the attachment points of pusher elements 30 and 32 to bands 34 and 36, respectively, are also provided as low as possible above (or in) the cervical zone so as to be as close as possible to the centers of resistance of teeth 38 and 40. As recognized in the '520 patent, this arrangement largely suppresses those components of the distalizing force exerted by pusher elements 30 and 32 which otherwise would act to tilt teeth 38 and 40 from their correct vertical orientations.

To prevent pusher elements 30 and 32 from discharging any reactive forces on anchoring teeth 18 and 20, transverse anchoring wire 16 may be provided with a pair of respective force compensation means 50 and 52 (in the form of wire loops). Wire loops 50 and 52 are suitably elastically preloaded by the technician in the direction opposite to the reaction force components resulting from pusher elements 30 and 32 applying their desirable distalizing forces. To ensure that no reaction forces are exerted on the anchoring teeth 18 and 20, loops 50 and 52 must be carefully shaped to provide an offsetting bias force that is substantially the same magnitude but in the opposite direction as the anticipated reaction forces from pusher elements 30 and 32 acting against teeth 38 and 40 which are not absorbed by Nance button 14.

Another feature of distalizing apparatus 10 disclosed in the '520 patent is that pusher elements 30 and 32 may be converted into a rigid (or inactive) state to prevent further application of distalizing forces. This makes it possible to use distalizing apparatus 10 as an anchoring structure or molar retainer once distalizing has been successfully completed and when it is necessary to move the anterior teeth toward the distalized teeth to close any space that has been created.

According to the '520 patent, this conversion may be accomplished by providing a slit (or notch) 54 in the end of tube 44 (see FIG. 3) so that it can be readily clamped to pusher pin 42 to prevent any relative sliding movement therebetween (see FIG. 4). The '520 patent also mentions that this conversion process can be accomplished by applying a cold-setting or photo-activated resin to the junction of pin 42 and tube 44. Although the distalizing appliance 10 of the '520 patent when converted into a molar retainer by either of the foregoing methods can be reversed to restore pusher elements 30 and 32 to their active (or force-applying) states, the apparatus 10 must generally be removed from the patient's mouth in order to do so.

In view of the forgoing, it is an object of the invention to implement an orthodontic distalizing apparatus which, like the devices disclosed in the '520 patent, effectively eliminates all the above-noted drawbacks of conventional distalizing devices, while at the same time offering greater ease of installation, adjustment and conversion between the active and passive states.

SUMMARY OF THE INVENTION

The invention achieves the aforesaid objects with an orthodontic distalizing apparatus comprising at least one force generating element positioned intermediate a force dissipating element secured to the hard palate and/or alveolar ridge and a first tooth (e.g., a molar) being distalized. The at least one force generating element is positioned to apply a distalizing force on the first tooth in a direction substantially along a longitudinal axis of the dental arch and a low level of the basal gingiva.

According to a first aspect of an embodiment of the present invention, the at least one force generating element is configured to prevent inadvertent disassembly thereof during installation, adjustment and/or conversion of the apparatus between an active and a passive state.

According to another aspect of an embodiment of the present invention, the at least one force generating element is reversibly convertible between the active and passive states while remaining installed in the patient's mouth.

According to a different aspect of an embodiment of the present invention, the force dissipating element is connected to at least one anchoring tooth different from the first tooth by a slidable coupling that absorbs all forces transmitted along a direction of the longitudinal arch.

According to a further aspect of an embodiment of the present invention, the at least one force generating element provides a continuous activation force of a substantially constant magnitude as the first tooth is distalized.

According to a yet another aspect of an embodiment of the present invention, a second force generating element may be positioned intermediate the force dissipating element and a second tooth (e.g., a bicuspid) for closing any gap that is created by distalization of the first tooth.

According to still another aspect of an embodiment of the present invention, a method for converting an orthodontic distalizing apparatus such as any of the foregoing between an active state and a passive state is also provided.

These and other benefits and features of the invention will be apparent upon consideration of the following detailed description of preferred embodiments thereof, presented in connection with the following drawings in which like reference numerals are used to identify like elements throughout.

BRIEF DESCRIPTION OF THE DRAWINGS

The particular characteristics of the invention and the advantages deriving from it will be evident in greater detail from the description of a preferred embodiment depicted as a non-limiting example in the attached drawings, in which:

FIG. 6 shows a second embodiment of an orthodontic distalizing apparatus in accordance with the present invention.

FIG. 7 shows an enlarged sectional view of the locking collar associated with the apparatus of FIG. 6.

FIG. 8 shows an enlarged sectional view of an alternative locking collar associated with the apparatus of FIG. 6.

Figure 1:
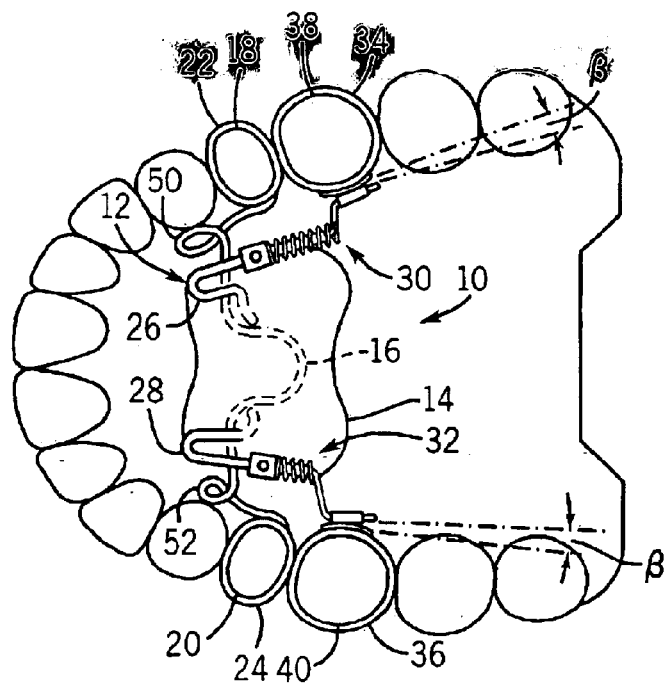
FIG. 1 shows a top view of a prior art apparatus applied to a dental arch.
Figure 2:
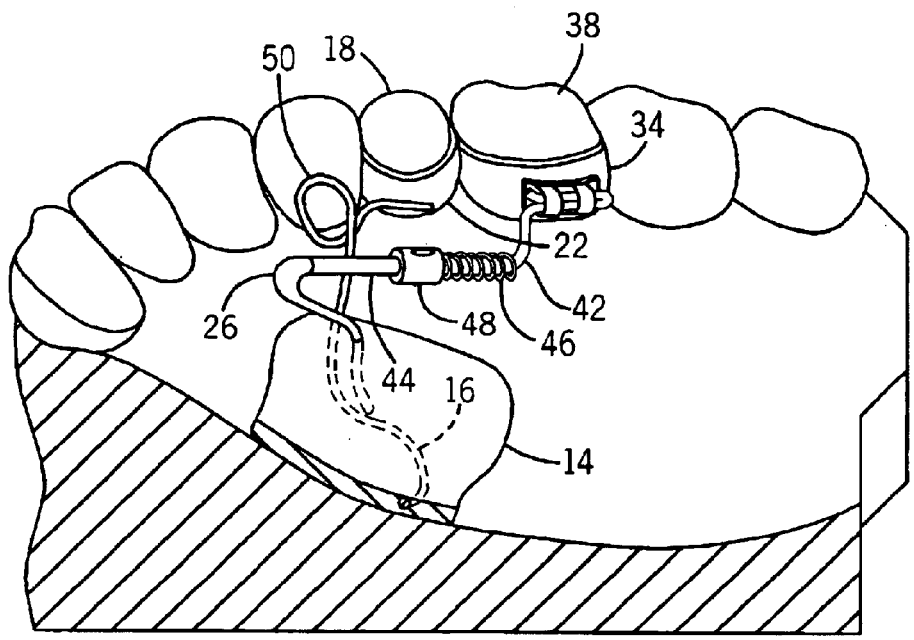
FIG. 2 shows a side elevation view of the prior art apparatus of FIG. 1.
Figure 3:
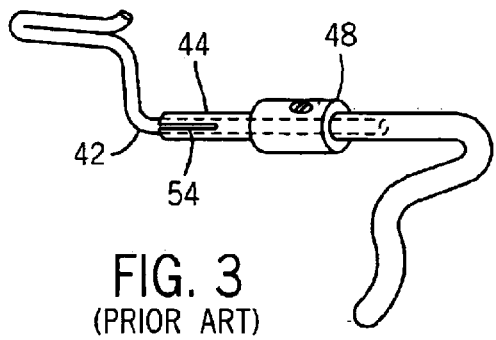
FIGS. 3 and 4 show an enlarged detail of the pusher elements of the prior art apparatus of FIG. 1 in two different operating states.
Figure 4:
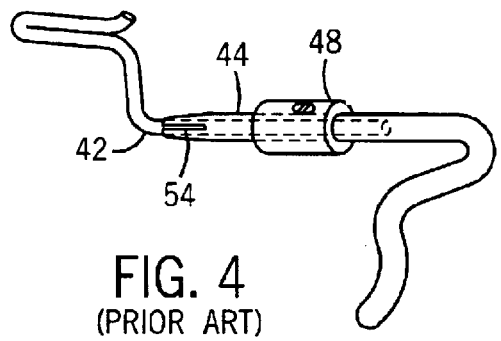

Before explaining at least one preferred embodiment of the invention in detail it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION OF THE PREFERRED EMBODIMENTS

Figure 5:
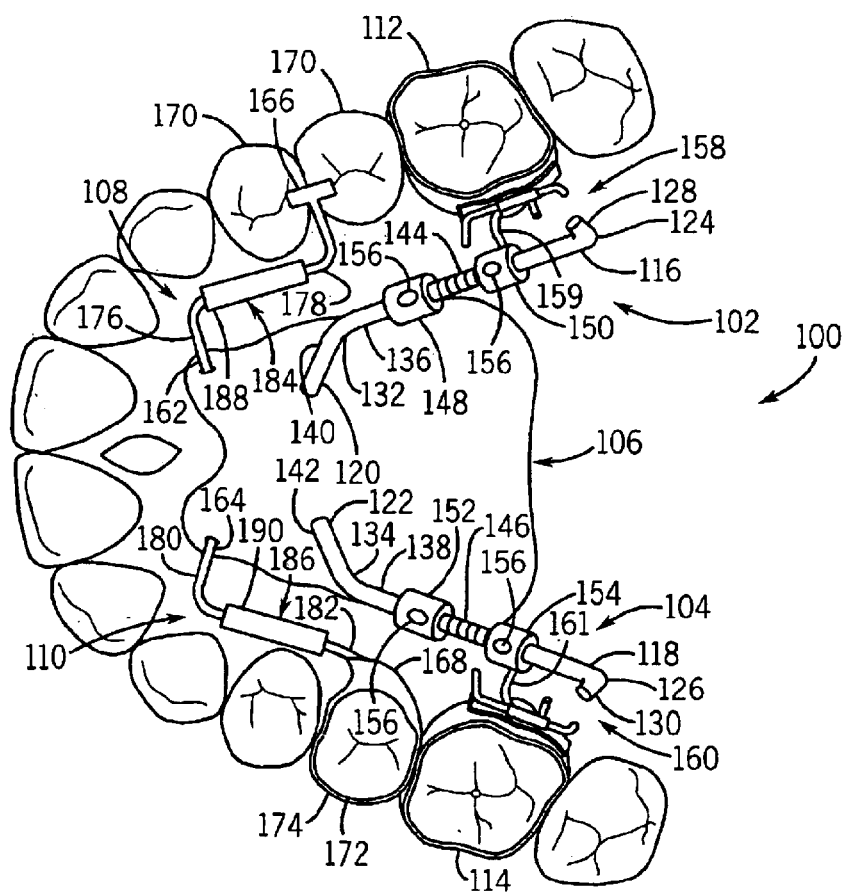
FIG. 5 shows a first embodiment of an orthodontic distalizing apparatus in accordance with the present invention.

Referring initially to FIG. 5, a first embodiment of an orthodontic distalizing apparatus 100 in accordance with the present invention is shown mounted to a maxillary jaw. As illustrated, apparatus 100 generally includes a pair of force generating elements 102 and 104, a force dissipating element 106 (e.g., a Nance button) configured for engaging the hard palate and/or alveolar ridge, and a pair of anchoring elements 108 and 110. Each force generating element is preferably positioned and oriented to apply a distalizing force to a respective molar 112, 114 in a direction substantially along a longitudinal axis of the dental arch and at a low level of the basal gingiva. As explained in the '520 patent, applying forces at this low level and orientation causes the tooth distalizing forces to pass as close as possible to the center points of resistance of the molar 112, 114 being distalized, which minimizes risk of any undesirable tilting occurring during distalization.

In the illustrated embodiment, each force generating element 102, 104 includes an elongated guiding element 116, 118, respectively. Each guiding element 116, 118 includes a respective mesial end 120, 122 which is embedded in force dissipating element 106 and a respective distal end 124, 126 having an associated distal stop 128, 130 located thereon. As illustrated, each guiding element 116, 118 may be formed from a solid, heavy wire (e.g., large diameter stainless steel), and each distal stop 128, 130 may be formed on its associated wire by simply bending or kinking the distal end 124, 126 thereof. If desired, an annealing process may be used to facilitate the bending of distal ends 124 and 126 to form distal stops 128 and 130 and, if so, the distal ends 124 and 126 may be doubled back upon themselves to provide a smooth surface. As discussed below in connection with the additional exemplary embodiments, distal stops 128 and 130 could take other forms as are well known in the art.

Preferably, each guiding element 116, 118 includes an additional bend or elbow 132, 134, respectively, that is located in a substantially vertically spaced relationship with (i.e., generally above or below, depending on whether apparatus 100 is situated on the mandible or maxilla) the entry point of each guiding element 116, 118 into force dissipating element 106. Thus, each guiding element 116, 118 may include a substantially horizontal main portion 136, 138 and a mesial portion 140, 142 having a substantially vertical component. As will be appreciated, the vertical component portions 140 and 142 of guiding elements 116 and 118 provide an improved geometry in that the reactive forces resulting from force generating elements 102 and 104 pushing against molars 112 and 114 are directed deeper into the palate than would be the case for a similar apparatus that is lacking such a vertical component. As a result of this structure, force dissipating element 106 is less likely to slip mesially (i.e., toward the front center of the mouth) than would otherwise be the case.

As illustrated in FIG. 5, each force generating element 102, 104 further comprises an associated compression spring 144, 146 which is slidably mounted on the associated guiding element 116, 118 along with a pair of adjustable spring stops 148, 150 and 152, 154, respectively, abutting against the anterior and posterior ends of each spring 144, 146, respectively. In a preferred embodiment, each spring stop 148, 150, and 152, 154 is releasably lockable in axial position along the horizontal portion 136 and 138, respectively, of the associated guiding element 116 and 118. In a particularly preferred embodiment, each spring stop 148, 150, 152 and 154 comprises a locking collar and a set screw 156 which allows the collar to be readily fixed in a position by rotating the screw in one direction or released and moved to a different position by rotating the screw in the opposite direction.

Still referring to FIG. 5, each posterior spring stop 150, 154 is fixedly connected to the associated molar 112, 114 to move therewith by means of a support linkage 158, 160. As illustrated, each support linkage 158, 160 may be formed of a relatively short and rigid lingual wire 159, 161 having one end attached (e.g., by means of soldering or welding) to the associated posterior spring stop 150, 154 and an opposite end attached (e.g., by means of a lingual tube and an associated band) to the associated molar 112, 114. Persons skilled in the art will recognize that support linkages 158 and 160 could take other forms besides simple wires and could be secured to the posterior collars and/or to the molars by other means, e.g., directly attached to the molars using an adhesive compound. Regardless of the particular structure and attachment means used for support linkage 158, 160, it can be seen that each force generating element 102, 104 is operatively positioned at a low level of the dental arch between force dissipating element 106 and the associated molar 112, 114 being distalized.

If desirable for the particular application at hand, force dissipating element 106 may be further secured in place by means of anchoring elements 108 and 110. As illustrated, each anchoring element 108, 110 includes an associated mesial end 162, 164 embedded in force dissipating element 106 and an associated distal end 166, 168 fixedly or releasably attached to an associated anchoring tooth (or teeth) 170, 172 (e.g., a bicuspid). In the particular embodiment illustrated in FIG. 5, distal end 166 of anchoring element 108 is secured to the crowns of two adjacent anchoring teeth 170 by use of an adhesive, while distal end 168 of anchoring element 110 is secured to anchoring tooth 172 by use of a soldered band 174.

In a preferred embodiment, each anchoring element 108, 110 may comprise a pair of wire segments 176, 178 and 180, 182, respectively, with the wire segments of each pair being joined together by a force absorbing coupling 184, 186, respectively. Each force absorbing coupling 184, 186 is designed to prevent transfer of substantially all the forces that are oriented in a direction substantially along the longitudinal direction of the arch, i.e., in a direction substantially parallel to the direction of distalization. Hence, any reaction forces that are imparted to force dissipating element 106 from the action of force generating elements 102 and 104 against molars 112 and 114 are not passed to anchoring teeth 170 and 172. In the illustrated embodiment, each force absorbing coupling 184, 186 comprises a slidable connection formed by a tubular cylinder 188, 190 having an anterior end soldered to wire segment 176, 180, respectively, and an opposite posterior end that slidably receives the other wire segment 178, 182, respectively. Persons skilled in the art will recognize that the various elements of force absorbing couplings 184 and 186 could be reversed from that illustrated, i.e., the posterior ends of the tubular cylinders could be soldered to the wire segments.

Now that the structure of distalizing apparatus 100 has been described in detail, a method of using apparatus 100 to distalize molars 112 and 114 will be provided. After mounting apparatus 100 in the maxillary or mandibular jaw, one or both of the force generating elements 102, 104 may be activated by moving the anterior spring stop(s) 148, 152 in a posterior direction (i.e., rearwardly or away from the front of the mouth) against the anterior end(s) of the associated compression spring(s) 144, 146 until the desired degree of compression has been achieved. Once this is done, the anterior spring stops(s) 148, 152 can be fixed in position (i.e., converted into a molar retainer) by turning the screw(s) 156 as appropriate to lock spring stop(s) 148, 152 in place. During this activation process, the technician need not be concerned with either of the force generating elements 102, 104 inadvertently coming apart because distal stop(s) 128, 130 prevent any such incident.

After distalization has been successfully completed, apparatus 100 can readily be converted into a molar retainer by simply tightening the screw(s) 156 of all four spring stops 148, 150, 152 and 154. Once this has been done, apparatus 100 will function as a Nance appliance anchored to molars 112 and 114, which thus permits selected anterior teeth to be moved toward the recently distalized teeth 112, 114 to close any spaces created during distalization. If desired, the technician can remove one or both anchoring elements 108, 110 when apparatus 100 is being used as a molar retainer.

Referring now to FIG. 6, a second embodiment of an orthodontic distalizing apparatus 200 is shown. For brevity, the description of distalizing apparatus 200 will be generally limited to its differences relative to distalizing apparatus 100 described above. For convenience, elements of distalizing apparatus 200 that are substantially similar to corresponding elements of distalizing apparatus 100 will be identified by the same reference numerals but preceded by a "2" instead of a "1".

Distalizing apparatus 200 differs from distalizing apparatus 100 described above in that each anterior spring stop 248, 252 comprises a generally cone-shaped collar 201 and a set screw 256. As best seen in FIG. 7, cone shaped collar 201 comprises a cylindrical base portion 203 and a conical portion 205. Conical portion 205 includes a threaded bore 207 which extends approximately perpendicular to the conical outer surface 217 and is thus at an angle relative to a central bore 209 that extends through collar 201 for slidably receiving one of the guiding elements 216, 218. As a result of this structure, the anterior spring stops 248 and 252— when slidably mounted on guiding element 216 and 218 with their respective conical portions 205 closest to the front of the mouth—are significantly easier to adjust in position because of the improved angle provided for accessing screws 256. FIG. 8 shows an alternatively shaped collar 201' which provides the same advantages as collar 201 but which requires less material for its manufacture. Collars 201 and 201' can be made by casting and/or machining as well as several other manufacturing techniques that are well known in the art.

Distalizing apparatus 200 also differs from distalizing apparatus 100 described above with respect to anchoring elements 208 and 210. Unlike anchoring elements 108, 110 described above, each anchoring element 208, 210 provides a rigid (i.e., non-force absorbing) connection between force dissipating element 206 and anchoring teeth 270 and 272. That is, anchoring elements 208 and 210 lack the slidable force absorbing coupling associated with anchoring elements 108 and 110 of apparatus 100 described above. Another difference is that the two anchoring elements 208 and 210 of apparatus 200 are secured to anchoring teeth 270 and 272, respectively, by means of a pair of soldered bands 274 rather than a combination of soldered bands and an adhesive.

Figure 9:
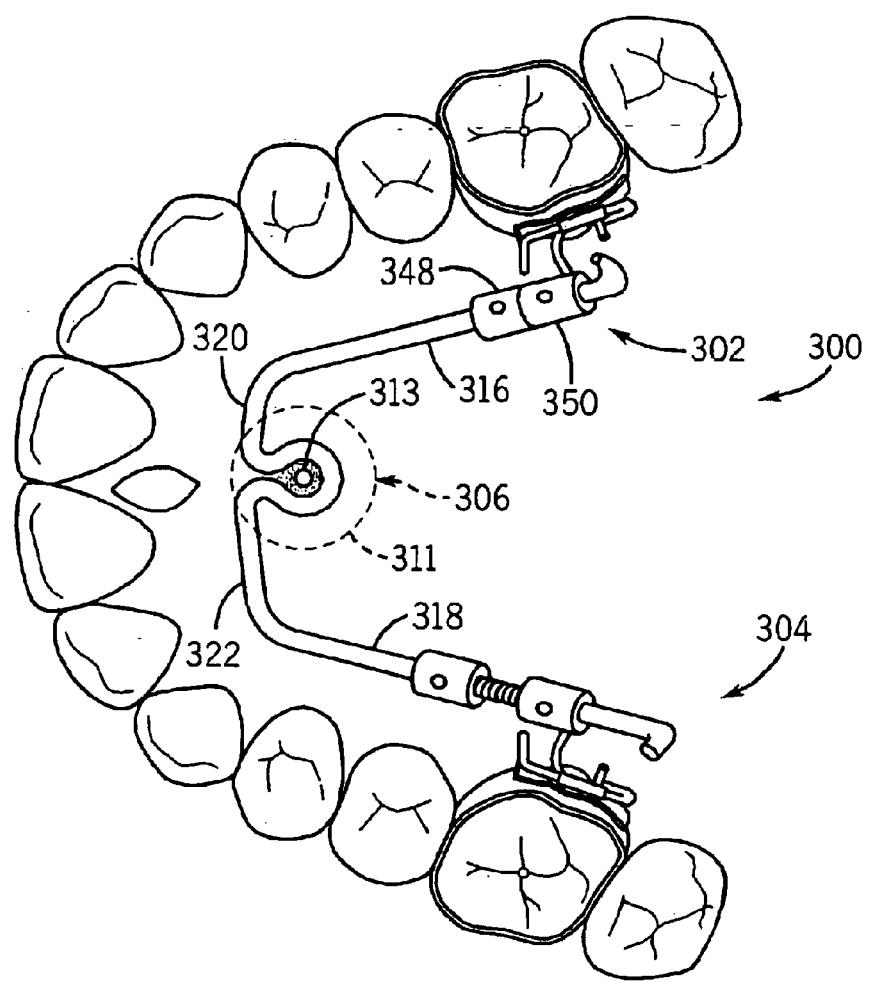
FIG. 9 shows a third embodiment of an orthodontic distalizing apparatus in accordance with the present invention.

Referring now to FIG. 9, a third embodiment of an orthodontic distalizing apparatus 300 is shown. For brevity, the description of distalizing apparatus 300 will be generally limited to its differences relative to distalizing apparatus 100 described above. For convenience, elements of distalizing apparatus 300 that are substantially similar to corresponding elements of distalizing apparatus 100 will be identified by the same reference numerals but preceded by a "3" instead of a "1".

Distalizing apparatus 300 differs from distalizing apparatus 100 described above in that force dissipating element 306 is in the form of an osseointegrated (e.g., subperiosteal or endosseous) implant 311. Implant 311, which resembles a button, is a relatively flat, disc-shaped fixture having a threaded aperture 313 for securing thereto the mesial ends 320, 322 of guiding elements 316, 318 or another transpalatal member. Implant 311 is known as an "indirect anchorage device," which is a term of art given to implants that are placed solely for orthodontic purposes (e.g., for stabilizing specific dental units to which clinical forces are then applied) and are generally removed once their anchorage duties have been fulfilled. Implant 311 provides for reliable anchorage and dissipation of the reactive forces generated by force generating elements 302 and 304 with no possibility of any anterior or mesial movement and no requirement of patient compliance or dexterity. Presently, there are at least two indirect implants available in the United States: a device known as the OnPlant, and another called the OrtoImplant.

Distalizing apparatus 300 also differs from distalizing apparatus 100 described above with respect to force generating element 302. Unlike force generating element 102 of apparatus 100 described above, force generating element 302 is shown in its inactive (or passive) state in which the compression spring has been removed and both collars 348, 350 have been locked in position. Thus, element 302 will function as a molar retainer. It should be noted that FIG. 9 is intended purely for purposes of illustration and that in actual use the technician would typically convert both force generating elements 302 and 304 to the rigid (or passive) state. It should also be noted that the compression spring can usually be readily removed by simply grasping one end of the spring with a pliers and pulling with sufficient force to cause the spring to unwind from guiding element 316.

Figure 10:
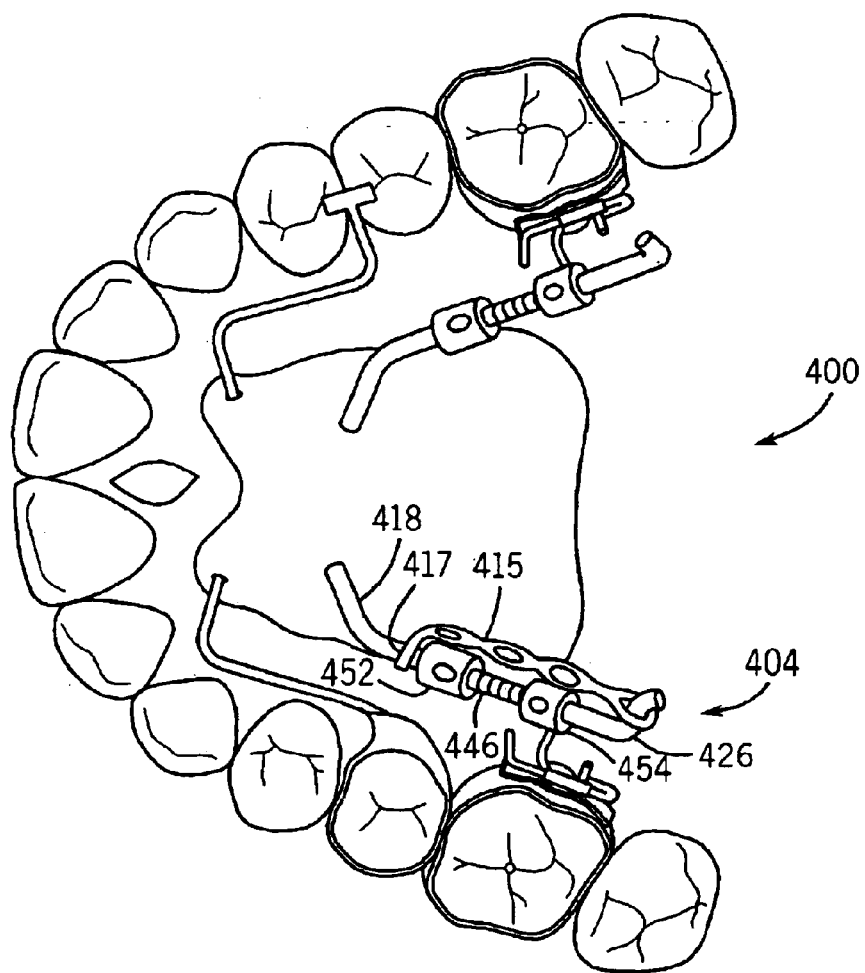
FIG. 10 shows a fourth embodiment of an orthodontic distalizing apparatus in accordance with the present invention.

Referring now to FIG. 10, a fourth embodiment of an orthodontic distalizing apparatus 400 is shown. For brevity, the description of distalizing apparatus 400 will be generally limited to its differences relative to distalizing apparatuses 100 described above. For convenience, elements of distalizing apparatus 400 that are substantially similar to corresponding elements of distalizing apparatus 100 will be identified by the same reference numerals but preceded by a "4" instead of a "1".

Distalizing apparatus 400 differs from distalizing apparatus 100 described above in that force generating element 404 has been modified to provide continuous force activation. More specifically, force generating element 404 has been modified relative to force generating element 104 of apparatus 100 in that anterior spring stop 452 is free floating (i.e., rather than fixed in one position) during distalization and that element 404 additionally includes an elastic strap (or chain) 415. As illustrated, elastic strap 415 is stretched (or tensioned) between the medial face of anterior spring stop 452 and the distal end 426 of guiding element 418. Although strap 415 is illustrated with its anterior-most loop 417 extending around wire 418, loop 417 could instead be secured directly to collar 452. One way this could be accomplished would be to substitute for collar 452 a collar similar to locking collar 652A (see FIGS. 13 and 14) which provides a convenient tie off 655 (as described in detail below).

Returning now to FIG. 10, elastic strap 415 applies a force in a posterior direction to anterior spring stop 452 that directly opposes the force applied in an anterior direction to anterior spring stop 452 by compression spring 446. With these two opposing forces in equilibrium, elastic strap 415 will compress anterior spring stop 452 in a posterior direction against compression spring 446 to drive posterior spring stop 454 distally to cause spring 446 to remain continuously in a (nearly) fully compressed state. That is, so long as elastic strap 415 retains its memory, force generating element 404 will continue to provide its full distalizing force regardless of how far molar 414 moves in a posterior direction during distalization. Once again, it should be noted that FIG. 10 is intended solely for purposes of illustration and that apparatus 400 when used in actual practice by a technician would be modified to include the elastic strap 415 on both of the force generating elements 402 and 404.

Figure 11:
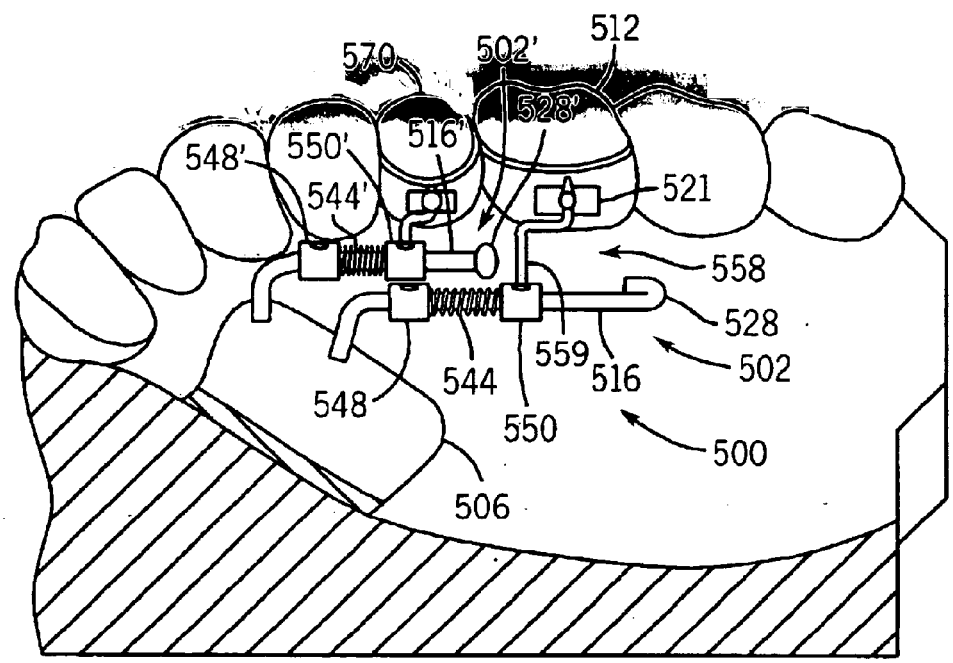
FIGS. 11 and 12 show a fifth embodiment of an orthodontic distalizing apparatus in accordance with the present invention.
Figure 12:
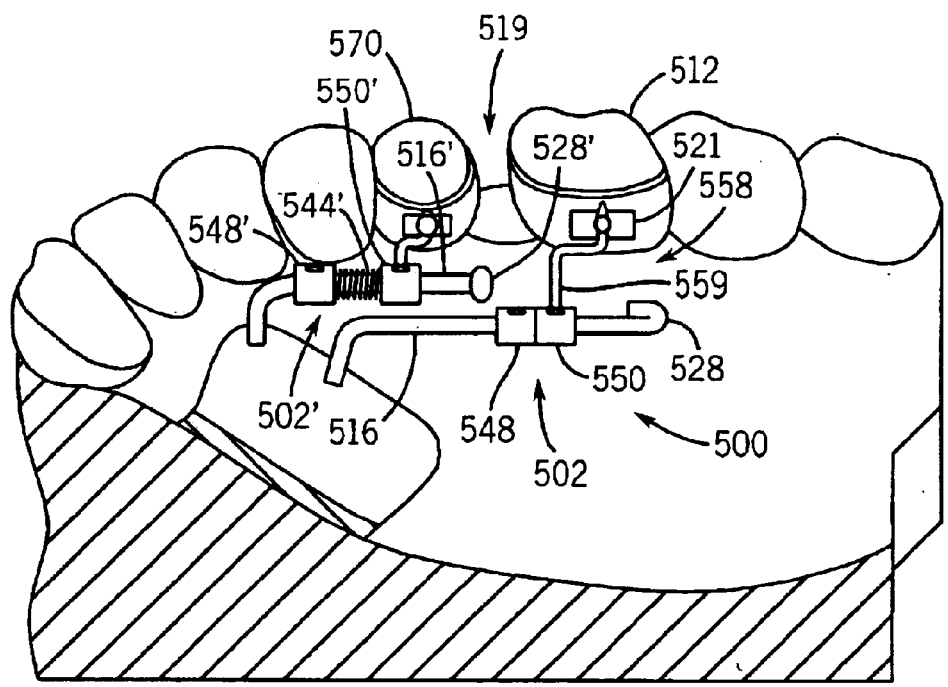

Referring now to FIGS. 11 and 12, a fifth embodiment of an orthodontic distalizing apparatus 500 is shown. For brevity, the description of distalizing apparatus 500 will be generally limited to its differences relative to distalizing apparatus 100 described above. For convenience, elements of distalizing apparatus 500 that are substantially similar to corresponding elements of distalizing apparatus 100 will be identified by the same reference numerals but preceded by a "5" instead of a "1".

Distalizing apparatus 500 differs from apparatus 100 in that in place of anchoring element 108 in apparatus 100, apparatus 500 includes a force generating element 502'. Although not illustrated, apparatus 500 also includes a similar force generating element on the opposite side of the dental arch in place of anchoring element 110 in apparatus 100. Thus apparatus 500 includes a first pair of force generating elements 502 positioned between force dissipating element 506 and molars 512, and a second pair of force generating elements 502' positioned between force dissipating element 506 and bicuspid 570. Each force generating element 502, 502' includes an associated spring 544, 544' captured between an anterior spring stop 548, 548' and a posterior spring stop 550, 550'. In addition, each force generating element 502, 502' includes an associated distal stop 528, 528'. In the illustrated embodiment, distal stop 528 is formed as a double-back and distal stop 528' is formed by a solder ball.

With the foregoing arrangement, apparatus 500 can be utilized in a two step method to first distalize molars 512 and, subsequently, to close any gaps that are created. In the first step, spring stops 548, 548' and 550' are moved to their desired positions and then fixed in place, while posterior spring stop 550 of thrust generating element 502 is allowed to freely slide along guiding element 516. Because spring stops 548' and 550' of force generating element 502' are both fixed in position, force generating element 502' will function as an anchoring element (or retainer) during this first step. By contrast, because spring stop 550 of force generating element 502 is not fixed in position, the biasing force provided by compression spring 544 will cause molar 512 to distalize and thus create a space (or gap) 519 between molar 512 and bicuspid 570 (see FIG. 12). According to a second step, space 519 can be closed (or reduced) by distalizing bicuspid 570 toward molar 512. This may be accomplished using apparatus 500 by fixing the position of posterior spring stop 550 of thrust generating element 502 while also unlocking posterior spring stop 550' of thrust generating element 502' so that it is free to slide along elongated guiding element 516'. Thus, the biasing force provided by compression spring 544' will cause bicuspid 570 to distalize toward molar 512, while at the same time thrust generating element 502 will function as an anchoring element. After bicuspid 570 has been sufficiently distalized to close (or reduce) space 519, posterior spring stop 550' of thrust generating element 502' can again be fixed in position to place apparatus 500 in its inactive state.

Apparatus 500 also differs from apparatus 100 in the attachment of support linkage 558 to molar 512. In particular, support linkage 558 includes a short and rigid lingual wire 559 that has one of its ends attached to molar 512 by means of a lingual sheath 521 oriented generally transverse to the longitudinal axis of elongated guiding element 516. As such, support linkage 558 can easily be decoupled from molar 512 by simply grasping wire 559 with a pliers and pulling downward with sufficient force to remove the end of wire 559 from lingual sheath 521. This facilitates adjustment of apparatus 500 and/or replacement of one or more of its elements after it has been installed in the patient. If desired, the end of wire 559 may have a square cross-section to facilitate its connection to lingual sheath 521. A similar releasable coupling arrangement may be provided between collar 548' and bicuspid 570.

Figure 13:
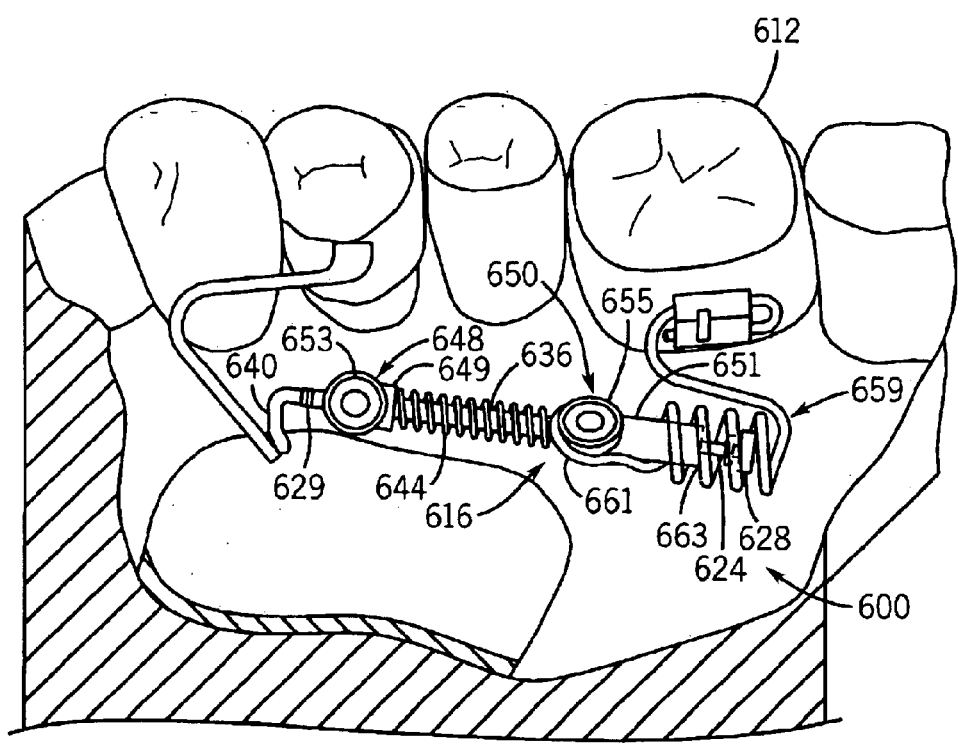
FIG. 13 shows a sixth embodiment of an orthodontic distalizing apparatus in accordance with the present invention.
Figure 14:
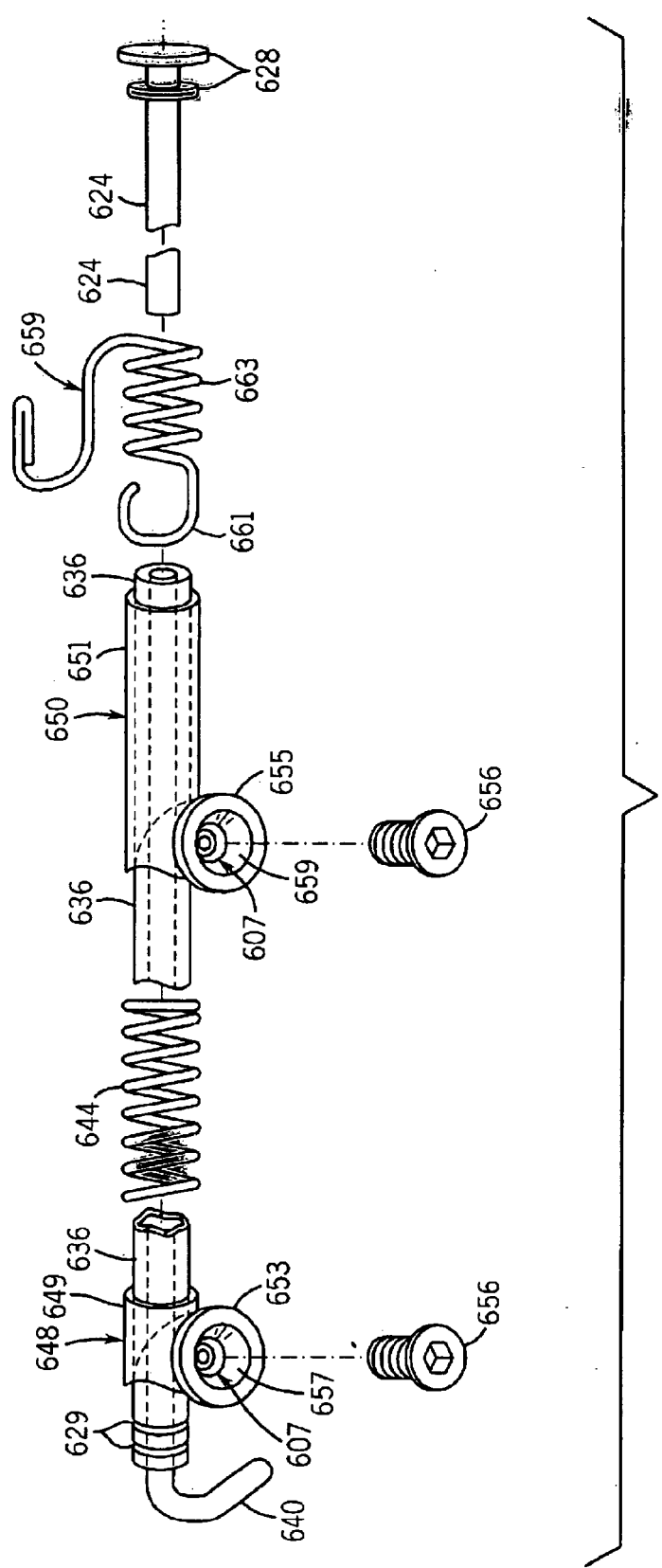
FIG. 14 shows an enlarged, exploded perspective view of a force generating element and an associated support linkage of the apparatus of FIG. 13.

Referring now to FIGS. 13 and 14, a sixth embodiment of an orthodontic distalizing apparatus 600 is shown. For brevity, the description of distalizing apparatus 600 will be generally limited to its differences relative to distalizing apparatus 100 described above. For convenience, elements of distalizing apparatus 600 that are substantially similar to corresponding elements of distalizing apparatus 100 will be identified by the same reference numerals but preceded by a "6" instead of a "1".

Distalizing apparatus 600 differs from apparatus 100 in that in place of the solid, fixed length guiding element 116 and the short, rigid lingual wire 159 of apparatus 100, apparatus 600 includes a multi-piece, expandable length guiding element 616 and an elongated, coiled support linkage 659, respectively. In addition, apparatus 600 includes alternative locking collars 648 and 650 which, as described more fully below, include a number of features not present in collars 148 and 150 of apparatus 100.

According to the illustrated embodiment, elongated guiding element 61 6 comprises a mesial portion 640 formed by a solid, heavy gauge (i.e., large diameter) wire, a substantially horizontal main portion 636 formed by a hollow tube, a distal end 624 configured to be slidably received within the interior of hollow tube 636, and a distal stop 628 formed on distal end 624 by a double (asymmetric) nail-head end. Solid rod 640 may have its posterior end slidably received within the anterior end of hollow tube 636, and the two ends may be coupled together by laser welding 629.

In an exemplary embodiment, each locking collar 648, 650 includes a cylindrical base portion 649, 651, respectively, and a transversely extending screw receiving portion 653, 655, respectively. As best illustrated in FIG. 14, each screw receiving portion 653, 655 may include a funnel-shaped opening 657, 659 that leads to a threaded bore 607 for facilitating the reception of a set screw 656 therein. As best illustrated by FIG. 13, each screw receiving portion 653, 655 has an exterior cylindrical surface that provides a convenient tie off location for a ligature wire, elastic strap, or any other orthodontic element without requiring a permanent connection. For example, coiled support linkage wire 659 is illustrated with a mesial portion 661 tied off to screw receiving portion 655 of collar 650. Because support linkage wire 659 is tied to collar 650 rather than permanently fastened (e.g., welded) thereto, wire 659 can be easily decoupled from collar 650 to facilitate adjustment thereof. As illustrated, support linkage wire 659 also includes a central coiled portion 663 extending around (and thus coupled to) distal stop 628 of movable distal end 624, as well as a distal end 665 that is releasably secured to molar 612 by a lingual sheath and a band. Central portion 663 may also include one or more loops extending around the elongated cylindrical base portion 651 of locking collar 650.

With the foregoing structure, persons skilled in the art will recognize that guiding element 616 has an adjustable length. In particular, the length of guiding element 616 will vary in accordance with the amount or distance that molar 612 is distalized. More specifically, when collar 648 is locked and collar 650 is unlocked, compression spring 644 will cause collar 655 to move in a posterior direction along the exterior of hollow tube 636. As collar 650 continues to move in a posterior direction, it will eventually extend beyond the posterior end of hollow tube 636 and abut against the anterior-most flange or head on distal stop 628. Once this occurs, any additional posterior movement of collar 650 resulting from further expansion of compression spring 644 will cause distal end 624 to withdraw out of the interior of hollow tube 636 and thus effectively lengthen guiding element 616. Thus, apparatus 600 is advantageous in applications where space is at a premium because the length of guiding element 616 will be only as long as necessary to accomplish the distalization. Hence, apparatus 600 is less likely to interfere with swallowing or cause any other discomfort to the patient.

Persons skilled in the art will also recognize that the coiled shaped of support linkage 658 provides several advantages over a relatively short, straight wire. For example, the coiled shape of lingual wire 659 increases the length of support linkage 658 which provides it with a longer lever action when it is desirable to torque or rotate molar 612. As another example, the coiled shape of lingual wire 659 allows the technician to increase the effective distalization range of apparatus 600 by uncoiling wire 659 as desired.

Figure 15:
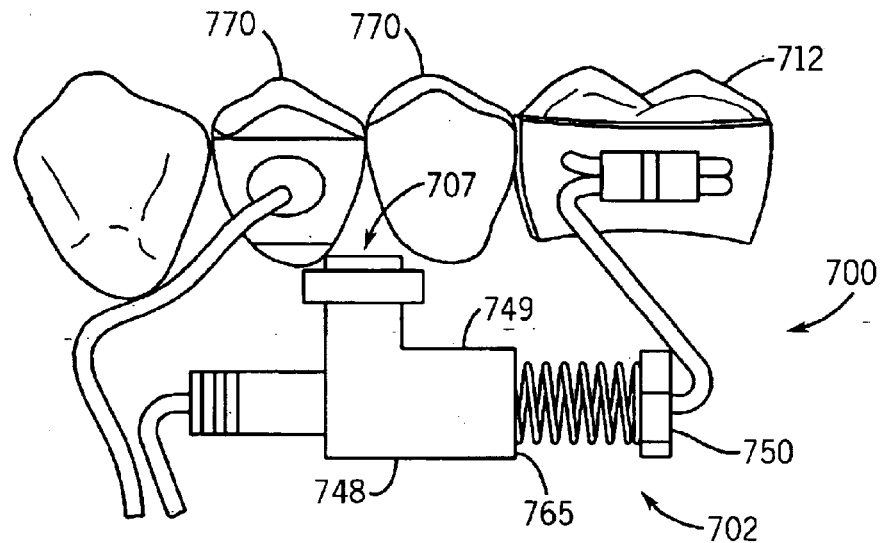
FIGS. 15 and 16 show a seventh embodiment of an orthodontic distalizing apparatus in accordance with the present invention.
Figure 16:
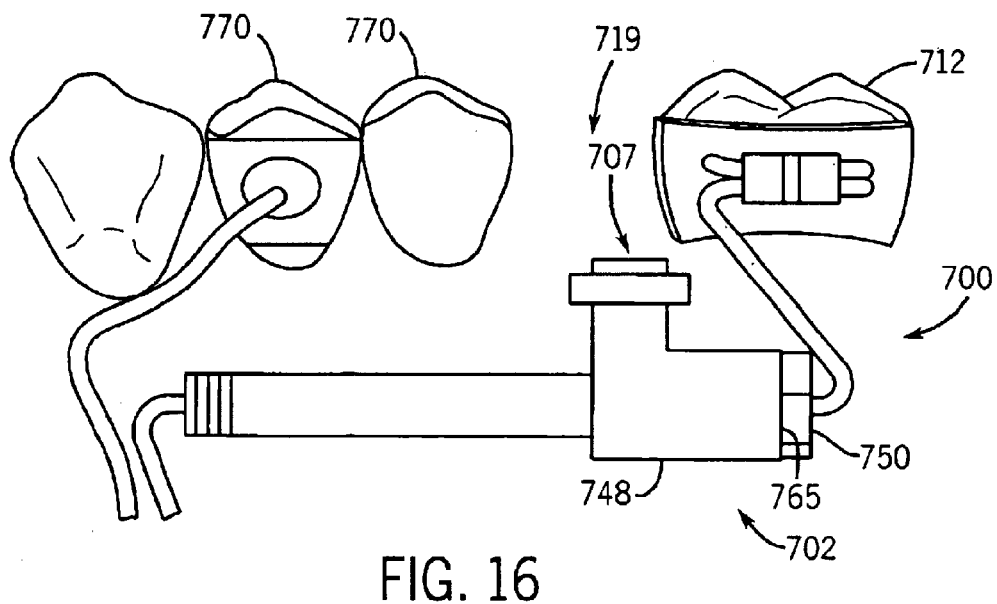

Referring now to FIGS. 15 and 16, a seventh embodiment of an orthodontic distalizing apparatus 700 is shown. For brevity, the description of distalizing apparatus 700 will be generally limited to its differences relative to distalizing apparatus 600 described above. For convenience, elements of distalizing apparatus 700 that are substantially similar to corresponding elements of distalizing apparatus 600 will be identified by the same reference numerals but preceded by a "7" instead of a "6".

Distalizing apparatus 700 differs from apparatus 600 in that force generating element 702 includes an anterior locking collar 748 that is elongated and a posterior collar (or spring stop) 750 that is non-lockable. According to an exemplary embodiment, anterior locking collar 748 includes a cylindrical base portion 749 having a mesio-distal length of about 7 mm when measured from the center of a central threaded bore 707 to a posterior edge 765. In addition, posterior spring stop 750 has a mesio-distal length of about 0.5 mm. As persons skilled in the art will recognize, the first and second bicuspids 770 of adult humans measure on average about 7.2 mm and 6.8 mm, respectively, taken along a mesio-distal line through the crowns. See Black, O. V., "Descriptive Anatomy of the Human Teeth," ed. 4, Philadelphia, Pa., 1897, The S.S. White Dental Manufacturing Co. Quite commonly, a molar 712 needs to be distalized because it has encroached in the anterior bicuspid space (i.e., moved forwardly into the arch). Thus, it will be appreciated by persons skilled in the art that anterior locking collar 748 has a length substantially equal to the maximum mesio-distal length of a space (or gap) 719 that is likely to be created during distalization. With the forgoing construction, it is possible to quickly convert force generating element 702 into a rigid, mechanically fixed retainer after distalization is complete by removing spring 744 and sliding anterior locking collar 748 in a posterior direction until it abuts posterior collar 750, and then locking anterior 748 collar in place.

It is important to note that the above-described preferred embodiments of the distalizing apparatuses are illustrative only. Although the invention has been described in conjunction with specific embodiments thereof, those skilled in the art will appreciate that numerous modifications are possible without materially departing from the novel teachings and advantages of the subject matter described herein. For example, although each distalizing apparatus disclosed and illustrated above includes a pair of force generating elements, only one force generating element need be used if the molar(s) requiring distalization are all on the same side of the dental arch. In addition, although the apparatuses are all shown being anchored to bicuspids, other teeth including incisor, canines or other molars could be used as an anchoring teeth if desired. Accordingly, these and all other such modifications are intended to be included within the scope of the present invention. Other substitutions, modifications, changes and omissions may be made in the design, operating conditions and arrangement of the preferred and other exemplary embodiments without departing from the spirit of the present invention.

What is claimed is:

1. An orthodontic apparatus for distalizing a first tooth of a dental arch, comprising:
    a force dissipating element configured to be located on a bony support of the dental arch; and
    at least one force generating element configured to be positioned intermediate the force dissipating element and the first tooth, wherein the at least one force generating element is configured to be positioned to apply a distalizing force on the first tooth in a direction substantially along a longitudinal axis of the dental arch and at a low level of the basal gingiva, and wherein the at least one force generating element is configured to prevent inadvertent disassembly thereof during installation, adjustment or conversion of the apparatus between an active and a passive state, and wherein the at least one force generating element includes an elongated guiding element along with a compression spring and a pair of spring stops slidably mounted thereon, the compression spring being captured between the spring stops.

2. The apparatus of claim 1, wherein the force dissipating element is a Nance button.

3. The apparatus of claim 1, wherein the force dissipating element is a dental implant.

4. The apparatus of claim 1, wherein the force dissipating element is secured in place by an anchoring element configured to extend between the force dissipating element and at least one anchoring tooth that is different from the first tooth.

5. The apparatus of claim 4, wherein the at least one anchoring tooth comprises a bicuspid and the first tooth comprises a molar.

6. The apparatus of claim 4, wherein the anchoring element includes a force absorbing coupling configured to prevent transfer of substantially all reactive distalizing forces oriented along the longitudinal direction of the dental arch.

7. The apparatus of claim 6, wherein the force absorbing coupling includes a slidable connection.

8. The apparatus of claim 4, wherein the anchoring element comprises a second force generating element that is in an inactive state.

9. The apparatus of claim 1, wherein each spring stop is adjustable and lockable in position.

10. The apparatus of claim 1, wherein the elongated guiding element includes a distal stop that prevents removal of the compression spring and the pair of spring stops in a posterior direction.

11. The apparatus of claim 10, wherein the distal stop is selected from a double-back, a solder ball, a bend, a nailhead, and an object that is releasably or permanently secured to the distal end of the elongated guiding element.

12. The apparatus of claim 1, wherein the pair of spring stops comprises an anterior locking collar and a posterior collar, the anterior locking collar being fixed in position during distalization and the posterior collar being freely slidable along the elongated guiding element during distalization.

13. The apparatus of claim 12, wherein the posterior collar is configured to be releasably coupled to the first tooth by a lingual wire having an end portion secured in a lingual sheath oriented in a direction substantially transverse to the elongated guiding element.

14. The apparatus of claim 12, wherein the elongated guiding element comprises a hollow tube having a distal end slidably received therein to provide the elongated guiding element with an adjustable length.

15. The apparatus of claim 14, wherein the posterior collar is configured to be releasably coupled to the first tooth by a support linkage having a coiled portion coupled to a distal stop formed on the distal end.

16. The apparatus of claim 12, wherein the anterior locking collar has a substantially conical outer surface facing in a mesial direction.

17. The apparatus of claim 1, wherein the elongated guiding element is a solid rod.

18. The apparatus of claim 1, wherein the elongated guiding element is a multi-piece structure having a length that varies in accordance with the distalization of the first tooth.

19. The apparatus of claim 1, wherein at least one of the spring stops comprises a locking collar having a cylindrical base portion and a transversely extending screw receiving portion.

20. The apparatus of claim 19, wherein the cylindrical base portion has a mesio-distal length about equal to an expected maximum distalization distance of the at least one tooth.

21. The apparatus of claim 1, wherein the elongated guiding element has a substantially vertical orientation proximate the force dissipating element.

22. An orthodontic apparatus for distalizing a first tooth of a dental arch, comprising:
    a force dissipating element configured to be located on a bony support of the dental arch; and
    at least one force generating element configured to be positioned intermediate the force dissipating element and the first tooth, wherein the at least one force generating element is configured to be positioned to apply a distalizing force on the first tooth in a direction substantially along a longitudinal axis of the dental arch and at a low level of the basal gingiva, and wherein the at least one force generating element is configured to be reversibly convertible between an active state and a passive state while remaining installed in the dental arch, and wherein the at least one force generating element includes an elongated guiding element on which are mounted a compression spring and a pair of spring stops, the compression spring being captured between the spring stops, and wherein the pair of spring stops comprises an anterior locking collar and a posterior locking collar, the posterior locking collar being unlocked to configure the apparatus for the active state and locked to configure the apparatus for the passive state.

23. The apparatus of claim 22, wherein the anterior locking collar remains locked during both the active and passive states.

24. The apparatus of claim 22, wherein the apparatus is configured to distalize the first tooth when in the active state and to act as a retainer for the first tooth when in the passive state.

25. The apparatus of claim 22, wherein the elongated guiding element is a solid rod.

26. The apparatus of claim 22, wherein the elongated guiding element is a multi-piece structure having a length that varies in accordance with the distalization of the first tooth.

27. The apparatus of claim 22, wherein the first tooth is a molar.

28. An orthodontic apparatus for distalizing a first tooth of a dental arch, comprising:
   a force dissipating element configured to be located on a bony support of the dental arch;
   at least one force generating element configured to be positioned intermediate the force dissipating element and the first tooth, wherein the at least one force generating element is configured to be positioned to apply a distalizing force on the first tooth in a direction substantially along a longitudinal axis of the dental arch and at a low level of the basal gingiva; and
   an anchoring element for securing the force dissipating element in place, the force dissipating element being configured to be connected to at least one anchoring tooth different from the first tooth by a force absorbing coupling that absorbs all forces transmitted substantially along a longitudinal direction of the dental arch, wherein the force absorbing coupling includes a slidable connection.

29. The apparatus of claim 28, wherein the slidable connection is formed by a tubular member configured to be fixedly connected to one of the force dissipating elements and the at least one anchoring tooth and a rod member slidably received in the tubular member and configured to be fixedly connected to the other of the force dissipating element and the at least one anchoring tooth, the slidable coupling being oriented in a direction substantially parallel to the longitudinal direction of the dental arch.

30. The apparatus of claim 28, wherein the anchoring element includes a distal end that is connected to the at least one anchoring tooth by soldering or an adhesive.

31. The apparatus of claim 28, wherein the anchoring element includes a distal end that is releasably secured to the at least one anchoring tooth by a lingual sheath and a band.

32. The apparatus of claim 28, wherein the first tooth is a molar.

33. A method for converting an orthodontic apparatus for distalizing a first tooth of a dental arch between a passive state and an active state, the apparatus distalizing the first tooth when in the active state and retaining the first tooth in position when in the passive state, the apparatus including a first force generating element positioned between a force dissipating element located on a bony support of the dental arch and the first tooth, the first force generating element including a first elongated guiding element on which are mounted a compression spring positioned between anterior and posterior lockable spring stops, the method comprising:
   unlocking the posterior spring stop to place the apparatus in the active state for distalization of the first tooth; and
   locking the posterior spring stop after distalization of the first tooth is completed to place the apparatus in the passive state for retaining the first tooth in position.

34. The method of claim 33, further including unlocking the posterior spring stop to reinitiate distalization of the first molar.

35. The method of claim 33, wherein the orthodontic apparatus further includes a second force generating element positioned between the force generating element and a second tooth on the same side of the arch as the first tooth but different from the first tooth, the second force generating element including a second elongated guiding element on which are mounted a compression spring positioned between anterior and posterior lockable spring stops, the method further comprising:
   locking the posterior spring stop on the second guiding element prior to distalization of the first tooth to anchor the force dissipating element in position during distalization of the first tooth.

36. The method of claim 35, further comprising:
   unlocking the posterior spring stop on the second guiding element after distalization of the first tooth is completed to distalize the second tooth.

37. The method of claim 35, wherein the first tooth is a molar and the second tooth is a bicuspid.

\* \* \* \* \*